United States Patent [19]

Vihko

[11] 4,205,130
[45] May 27, 1980

[54] METHOD OF PURIFICATION OF HUMAN PROSTATIC ACID PHOSPHATASE

[76] Inventor: Pirkko Vihko, Jaakonkuja 1 E 3, 90230 Oulu 23, Finland

[21] Appl. No.: 19,644

[22] Filed: Mar. 12, 1979

[51] Int. Cl.$^2$ ............................................. B01D 15/08
[52] U.S. Cl. ................................ 435/196; 210/31 C; 435/815
[58] Field of Search .................... 210/31 C; 23/230 B; 435/196, 815

[56] References Cited

U.S. PATENT DOCUMENTS

| | | | |
|---|---|---|---|
| 3,901,763 | 8/1975 | Horiuchi et al. | 435/196 |
| 3,947,352 | 3/1976 | Cuatrecasas et al. | 210/31 C |
| 4,166,766 | 9/1979 | Metzenberg et al. | 435/815 |

*Primary Examiner*—John Adee
*Attorney, Agent, or Firm*—Haseltine, Lake & Waters

[57] ABSTRACT

A new method of purification of human prostatic acid phosphatase has been provided. The starting point for the purification process is constituted by a solution containing acid phosphatase and having its origin in a sample derived from a human body. If required, said sample is subjected to a pretreatment so as to draw the phosphatase into solution and to remove any solid tissues. The solution is then treated by means of affinity chromatography, whereby the phosphatase in question is separated from other proteins. The chromatographic step is performed in a column packed with an agarose gel coupled with tartrate groups. A sodium acetate buffer containing tartrate may be used as an eluent and the eluate is collected as successive fractions. Those fractions containing the phosphatase are further treated by means of isoelectric focusing so as to separate the different isoenzymes of the phosphatase from each other. The isoelectric focusing may be performed either in a column or on a disc covered with a gel.

10 Claims, No Drawings

METHOD OF PURIFICATION OF HUMAN PROSTATIC ACID PHOSPHATASE

BACKGROUND OF THE INVENTION

The present invention relates to purification of human prostatic acid phosphatase including separation of the different isoenzymes of the phosphatase from each other. The phosphatase in question is of particular significance in connection with the diagnosis of prostatic diseases.

Estimation of acid phosphatase activity (orthophosphoric-monoester phosphohydrolase) in serum has served in the diagnosis of the prostatic carcinoma since the report by Gutman et al. in J.Clin. Invest., vol 17, p. 473 (1938). An increased total acid phosphatase activity in serum, has been observed in sera of patients with prostatic cancer. However, observations concerning the activities in sera, prostatic secretions, and tissue itself in relation to age, physiological atrophy, and pathological conditions have been inconsistent and largely contradictory. One reason for this may be the actual variations of enzyme activity, but it also seems that the prostatic enzyme is not specifically detected by the methods presently available.

It is apparent that satisfactory results in the diagnosis of prostatic diseases could be obtained by use of immunobiochemical applications. For this purpose it would be necessary to isolate an isoenzyme of the phosphatase in a highly pure condition. There have been purification procedures for prostatic acid phosphatase described in the prior art, these procedures comprising various precipitations and chromatographic steps. However, the results have not been completely satisfying with respect to the specific activity and recovery of the enzyme.

SUMMARY OF THE INVENTION

It is an object of the present invention to provide an improved method of purification of human prostatic acid phosphatase, which will yield an isoenzyme of acid phosphatase having a higher specific activity than isoenzymes purified in accordance with prior art methods.

A further object of the invention is to provide a method of purification of human prostatic acid phosphatase, which will yield an isoenzyme of said phosphatase with better recovery than before.

A still further object of the invention is to provide a purified isoenzyme, which will lend itself to the development of a highly specific antisera for radioimmunoassay.

In view of these and other objects of the invention, the method of purification of human prostatic acid phosphatase comprises a treatment of a solution containing said phosphatase by means of affinity chromatography as well as a subsequent treatment by means of isoelectric focusing. The chromatographic step is performed by introducing the solution into a column, which is packed with an agarose gel with tartrate groups. An eluent is then passed through the column and the eluate issuing from the column is collected as successive fractions. Preferably, a solution containing tartrate is used as the eluent and in the most preferred case the eluent is a sodium acetate buffer, in which tartrate has been dissolved. The division of the eluate into successive fractions isolates the phosphatase from other proteins that may be present in the solution that is subjected to the treatment. The isoelectric focusing is preferably carried out in a column and will divide the phosphatase into its isoenzymes.

Other objects and features of the invention will be apparent from the following detailed description of specific examples thereof.

EXAMPLE 1

Sample Handling Procedure

Fresh human prostatic tissue, obtained from surgery for prostatic hypertrophy, constituted the source of the enzyme. After excision, the gland was immediately frozen. The frozen prostate glands were sliced and homogenized (200 mg wet wt/ml) in distilled water. The homogenate was allowed to stand with occasional stirring for 30 min, rehomogenized, and centrifuged. The supernatant fluid was used. The supernate (45 ml) was 30% saturated with solid ammonium sulfate and centrifuged. The precipitate was discarded, and the supernatant fluid was 70% saturated with ammonium sulfate. After centrifugation, the precipitate was dissolved in 17 ml of distilled water and subsequently dialyzed for 16 h against 8 liters of sodium acetate buffer (50 mmol/liter, pH 5.0). The small amount of precipitate formed was removed by centrifugation.

Coupling of L(+)-Tartrate to Aminohexyl Agarose

L(+) Tartrate (E. Merck, Darmstadt) was coupled to aminohexyl agarose (AH-Sepharose 4B; Pharmacia Fine Chemicals AB, Uppsala, Sweden), as follows: 0.5 g of L(+)-tartrate was added to 50 g of wet gel. For the formation of amine bounds 1-ethyl-3(3-dimethylaminopropyl)-carbodiimide hydrochloride was used at a final concentration of 0.1 mol/liter. The gel was washed with NaHCO$_3$ buffer (0.1 mol/liter, pH 9.0) and sodium acetate buffer (0.1 mol/liter, pH 4.0, and containing 1 mol of NaCl per liter), alternately. Thereafter, the gel was packed into a glass column (Pharmacia, 45×16 mm). The concentration of L(+)-tartrate remaining in the column was 79 μmol/ml of AH-Sepharose 4B.

Affinity Chromatography

The column containing L(+)-tartrate linked to agarose was equilibrated with sodium acetate buffer (50 mmol/liter, pH 5.0) and 15 ml of the dialyzate containing 180 mg of protein per milliliter was applied onto the column, which then was washed with 20 ml of the equilibrating buffer. The enzyme was then eluted stepwise with 20-ml portions of the same buffer containing 10, 25, or 50 mmol of L(+)-tartrate per liter. Fractions of 2 ml were collected at a flow rate of 30 ml/h. Fractions corresponding to the second peak of protein with high enzyme activity were pooled. Of the pooled preparation, 10 ml was applied onto a Sephadex G-200 column (Pharmacia, 25×325 mm), which was equilibrated and eluted with tris(hydroxymethyl)methylamine acetate buffer (50 mmol/liter, pH 7.0). Fractions of 3 ml were collected at a flow rate of 20 ml/h. Those fractions representing the highest specific activity of acid phosphatase were pooled and subjected to isoelectric focusing.

Isoelectric Focusing

A sucrose gradient in an Ampholine 8100-1-column (LKB-Produkter AB, Stockholm) was used. The pH ranged from 3.5 to 10.0. A constant voltage of 300 V during the first 4 h and 800 V during the next 44 h was used. Thirty milliliters of sample was applied onto the column with a heavy sucrose solution and the cathode was used as the upper pole. Fractions of 2.5 ml were collected. There were two enzyme peaks, the one having the higher activity being at isoelectric point 4.9 and the one having the lower activity being at point 5.5. Those fractions representing the higher activity were pooled and applied onto a Sephadex G-50 column, to remove Ampholine and sucrose. The column (Pharmacia, 15×335 mm) was packed with Sephadex G-50, equilibrated with the tris (hydroxymethyl)methylamine acetate buffer, and eluted with equilibrating buffer. The sample was applied in 5 ml, and 4-ml fractions were collected; the flow rate was 25 ml/h. Fractions with high acid phosphatase activity were pooled, concentrated by ultrafiltration under nitrogen pressure, again passed through a Sephadex G-50 column, and reconcentrated.

Assays of Enzyme Activity

Acid phosphatase activity was assayed at 37° C. with 5.5 mmol/liter p-nitrophenyl phosphate as substrate in citrate buffer (50 mmol/liter, pH 4.8). After an incubation of 15 min, the reaction was stopped by adding 2 ml of a 0.02 mol/liter solution of NaOH, and the amount of p-nitrophenol liberated was measured. The method was adapted for a total volume of 220 $\mu$l (200 $\mu$l of substrate in buffer and 20 $\mu$l of sample). The enzyme activity was expressed in micromoles of p-nitrophenol split off by 1 ml of enzyme solution at 37° C. within 1 min ($\mu$mol/(min-ml) ). The specific activity was expressed as $\mu$mol (min-mg of protein).

RESULTS

The purification of the enzyme preparation is presented in Table 1. The specific activity of the enzyme preparation was about 2700 $\mu$mol/min×mg); and the analytical recovery of enzyme activity exceeded 15%. The purification factor is about 1300.

Table I

| Purification step | Total activity $\mu$mol/min | Specific activity $\mu$mol/(min × mg) | Recovery % | Purification factor |
|---|---|---|---|---|
| (NH$_4$)$_2$SO$_4$, 30–70% satn. | 5757 | 2.1 | 100 | 1 |
| AH-Sepharose 4B with L(+)-tartrate | 2586 | 162.6 | 45 | 77 |
| Sephadex G-200 | 2586 | 232.9 | 45 | 111 |
| Isoelectric focusing | 1475 | — | 26 | — |
| Sephadex G-50 | 1066 | 2665 | 19 | 1269 |

The results in table 1 represent a typical batch and it may be noted that in repeated experiments the recovery of enzyme activity always exeeded 15%. In the best cases the specific activity was about 4018 mol(-min×mg), which is to say that an approximately 1900-fold purification was obtained.

EXAMPLE 2

Human seminal fluid was used as the source of enzyme. It was diluted (1:1) with acetate buffer and centrifuged with ultracentrifuge (100000xg) for 30 min. The supernatant was treated further as described in example 1 for the enzyme from prostatic tissue.

EXAMPLE 3

The handling of the sample and the affinity chromatography were performed as described in example 1. The pooled fractions were subjected to disc electrophoresis by using 7.5% polyacrylamide gels with a tris (hydroxymethyl)methylamine-glycine buffer, pH 8.4. The separation time was 50 min, in which the phosphatase was divided into bands representing the different isoenzymes. These enzymically active bands in the gel were stained with $\alpha$-naphhyl phosphate coupled to Fast Garnet GBC.

While three specific embodiments of the invention have been described in detail above, it is to be understood that various modifications may be made from the specific details described without departing from the scope of the invention.

What is claimed is:

1. A method of purification of human prostatic acid phosphatase, which comprises the steps of:
    (a) treating a solution containing acid phosphatase by means of affinity chromatography by introducing said solution into a column packed with an agarose gel coupled with tartrate groups, by passing an eluent through said column and by collecting the eluate as successive fractions, and
    (b) subjecting a portion of the eluate containing said phosphatase to a further treatment by means of isoelectric focusing, whereby the phosphatase is divided into its isoenzymes.

2. a method as recited in claim 1, wherein the solution subjected to affinity chromatography is a sample derived from a human body and pretreated by removing any solid tissue material.

3. A method as recited in claim 1, wherein the agarose gel is aminohexyl agarose gel.

4. A method as recited in claim 1, wherein the eluent is a solution containing tartrate.

5. A method as recited in claim 4, wherein the eluent is a sodium acetate buffer containing tartrate and having a pH-value of about 5.0.

6. A method as recited in claim 1, wherein the fractions of the eluate are determined with respect to enzyme activity and the portion of the eluate subjected to isoelectric focusing is a combination of successive fractions representing a peak in said activity.

7. A method as recited in claim 1, wherein the isoelectric focusing is carried out in a column packed with filling material by introducing the portion of the eluate to be treated into the column, by applying an electric voltage between the ends of the column and by collecting the liquid issuing from the column as successive fractions.

8. A method as recited in claim 7, wherein said portion of the eluate is introduced into the column with a sucrose solution.

9. A method as recited in claim 8, wherein a fraction of the liquid passed through the column and containing one isoenzyme of the phosphatase is passed through another column so as to remove sucrose and residues of the filling material.

10. A method as recited in claim 1, wherein the isoelectric focusing is performed on a disc covered with a gel by introducing the portion of the eluate to be treated onto the disc and by applying an electric voltage between two poles on the disc, whereby the phosphatase is divided into separate zones between the poles, said zones representing the different isoenzymes of the phosphatase.

* * * * *